(12) United States Patent
Moon et al.

(10) Patent No.: US 10,799,477 B2
(45) Date of Patent: Oct. 13, 2020

(54) PHARMACEUTICAL COMPOSITION FOR PREVENTING OR TREATING LDL CHOLESTEROL-RELATED DISEASES, CONTAINING RIBOSOME-BINDING PREPARATION

(71) Applicant: PUSAN NATIONAL UNIVERSITY INDUSTRY UNIVERSITY, Busan (KR)

(72) Inventors: Yu Seok Moon, Gyeongsangnam-do (KR); Ju Il Kim, Gyeongsangnam-do (KR)

(73) Assignee: PUSAN NATIONAL UNIVERSITY INDUSTRY UNIVERSITY COOPERATION FOUNDATION, Busan (KR)

( * ) Notice: Subject to any disclaimer, the term of this patent is extended or adjusted under 35 U.S.C. 154(b) by 0 days.

(21) Appl. No.: 16/306,466

(22) PCT Filed: Jun. 1, 2017

(86) PCT No.: PCT/KR2017/005743
§ 371 (c)(1),
(2) Date: Nov. 30, 2018

(87) PCT Pub. No.: WO2017/209452
PCT Pub. Date: Dec. 7, 2017

(65) Prior Publication Data
US 2019/0183858 A1    Jun. 20, 2019

(30) Foreign Application Priority Data

Jun. 1, 2016 (KR) .................. 10-2016-0068306

(51) Int. Cl.
| | | |
|---|---|---|
| A61K 31/52 | (2006.01) | |
| A61P 9/10 | (2006.01) | |
| A61K 31/4015 | (2006.01) | |
| A23L 33/10 | (2016.01) | |
| A61K 31/352 | (2006.01) | |
| A61K 31/336 | (2006.01) | |
| A61K 31/40 | (2006.01) | |
| A61K 9/00 | (2006.01) | |

(52) U.S. Cl.
CPC .......... *A61K 31/4015* (2013.01); *A23L 33/10* (2016.08); *A61K 9/0053* (2013.01); *A61K 31/336* (2013.01); *A61K 31/352* (2013.01); *A61K 31/40* (2013.01); *A61P 9/10* (2018.01); *A23V 2002/00* (2013.01); *A23V 2200/3262* (2013.01)

(58) Field of Classification Search
CPC .. A61K 31/4015; A61K 31/336; A61K 31/40; A61K 38/45; A61K 31/7056; A61K 31/45; A61K 31/4745; A61K 31/7076; A61K 31/353; A61K 31/352; A61K 38/164; A61K 38/465; A61P 9/10; A61P 9/0053; A23L 33/10; A23V 2002/00; A23V 2200/3262; C07K 14/705; C12Y 204/02036; C12Y 301/2701
See application file for complete search history.

(56) References Cited

U.S. PATENT DOCUMENTS

| | | | |
|---|---|---|---|
| 6,756,410 B2 | 6/2004 | Mehta | |
| 8,067,022 B2* | 11/2011 | Kunz | A61K 9/0024 424/423 |
| 2004/0147557 A1 | 7/2004 | Bouillot et al. | |

FOREIGN PATENT DOCUMENTS

| | | | | |
|---|---|---|---|---|
| WO | WO-0101968 A2 * | 1/2001 | ........... | A61K 31/335 |
| WO | 2016/042318 A1 | 3/2016 | | |

OTHER PUBLICATIONS

Chen et al., "Mechanisms of dysregulation of low-density lipoprotein receptor expression in HepG2 cells induced by inflammatory cytokines"; Chinese Medical Journal 2007; vol. 120, No. 24 pp. 2185-2190.
Croons et al., "The Protein Synthesis Inhibitor Anisomycin Induces Macrophage Apoptosis in Rabbit Atherosclerotic Plaques through p38 Mitogen-Activated Protein Kinase"; The Journal of Pharmacology and Experimental Therapeutics, vol. 329, No. 3, pp. 856-864, 2009.
Dong et al., "CETP inhibitors downregulate hepatic LDL receptor and PCSK9 expression in vitro and in vivo through a SREBP2 dependent mechanism"; Atherosclerosis vol. 235 (2014), pp. 449-462.
Jeon et al., "Structure and Physiologic Function of the Low-Density Lipoprotein Receptor"; Annu. Rev. Biochem. 2005. vol. 74, pp. 535-562.

(Continued)

Primary Examiner — Sarah Pihonak
Assistant Examiner — Jason Deck
(74) Attorney, Agent, or Firm — Norris McLaughlin, P.A.

(57) ABSTRACT

The present invention relates to: a pharmaceutical composition for preventing or treating LDL cholesterol-related diseases, containing a ribosome-binding preparation; a food composition; and a method for preventing or treating LDL cholesterol-related diseases by using the composition. According to the present invention, the ribosome-binding preparation selectively increases the expression of an LDL receptor in intestinal epithelial cells so as to promote LDL absorption in blood and tissue, such that LDL level in the blood can be reduced, thereby being useful for preventing or treating various LDL cholesterol-related diseases including LDL hypercholesterolemia, hyperlipidemia, hypertension and apoplexy.

3 Claims, 14 Drawing Sheets
Specification includes a Sequence Listing.

(56) References Cited

OTHER PUBLICATIONS

Liu et al., "Reduced Macrophage Apoptosis Is Associated With Accelerated Atherosclerosis in Low-Density Lipoprotein Receptor-Null Mice"; Arteriosclerosis, Thrombosis, and Vascul Biol, 2005, vol. 25 pp. 174-179.
Makar et al., "Non-sterol regulation of low density lipoprotein receptor gene expression in T cells"; Journal of Lipid Research vol. 35,1994, pp. 1888-1895.
Zhou et al., "Direct Activation of Ribosome-Associated Double-Stranded RNA-Dependent Protein Kinase (PKR) by Deoxynivalenol, Anisomycin and Ricin: A New Model for Ribotoxic Stress Response Induction"; Toxins, 2014, vol. 6 pp. 3406-3425.
Zhou et al., "Blockage of oncostatin M-induced LDL receptor gene transcription by a dominant-negative mutant of C/EBPβ"; Biochem. J. (2006) vol. 397, pp. 101-108.

* cited by examiner

SEQUENCE LISTING

```
<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: LDLR shRNA

<400> SEQUENCE: 1
ggacagatat catcaacga                                              19
```

PHARMACEUTICAL COMPOSITION FOR PREVENTING OR TREATING LDL CHOLESTEROL-RELATED DISEASES, CONTAINING RIBOSOME-BINDING PREPARATION

This application is a 371 of PCT/KR2017/005743, filed Jun. 1, 2017, which claims foreign priority benefit under 35 U.S.C. § 119 of the Korean Patent Application No. 10-2016-0068306, filed Jun. 1, 2016, the disclosures of which are incorporated herein by reference.

TECHNICAL FIELD

The present disclosure relates to a composition for prevention or treatment of low-density lipoprotein (LDL) cholesterol-related diseases comprising a ribosome-binding agent, and to a method for preventing or treating low-density lipoprotein (LDL) cholesterol-related diseases using the composition.

BACKGROUND ART

Mammalian cells obtain cholesterol from two types of sources. A first source is lipoprotein particles, and a second source is free cholesterol. Absorption of the lipoprotein and free cholesterol is controlled to maintain homeostasis. Low-density lipoprotein (LDL) particles, as a major cholesterol transport vehicle include high concentrations of cholesterol. A human small intestine plays an important role in maintaining cholesterol balance. Accumulation of cholesterol in a cell membrane is toxic. Cholesterol absorption and storage are regulated by the small intestine to control the synthesis of cholesterol.

A LDL receptor (LDLR) is a transmembrane glycoprotein that plays a major role in the process of eliminating circulating cholesterol. The activity of the LDL receptor is known to be regulated by intracellular cholesterol levels. The LDL receptor plays a role in absorbing essential fatty acids and cholesterol into cells.

Vascular-related diseases such as heart diseases and cerebral vascular disease such as arteriosclerosis, cerebral hemorrhage, stroke, and cerebral infarction are adult diseases which are the first and second causes of death. These adult diseases frequently occur in middle-aged and elderly people due to changes in dietary patterns and internal and external environmental stresses as it has developed into modern society. The major cause of these diseases is known as thrombus. Thrombosis is recognized as pathological phenomenon mediated via excessive platelet aggregation. Platelets are activated by stimulation of various active substances such as collagen, thrombin, and ADP during vascular injury, thereby causing adhesion reaction, release reaction and aggregation reaction. Although these reactions are related to hemostasis, they play an important role in the development of blood vessel diseases that involve thrombosis.

Due to changes in lifestyle worldwide, LDL-related adult diseases and vascular diseases are increasingly on the rise. However, a fundamental therapeutic agent designed to treat the LDL-related diseases via adjustment of the LDL receptor has not yet been elucidated, and research therefor is needed.

DISCLOSURE

Technical Problem

The present inventors have conducted studies using a ribosome-binding agent to confirm that the ribosome inactivation increases the expression level of the LDL receptor, thereby promoting the absorption of LDL.

A purpose of the present disclosure is to provide a pharmaceutical composition for prevention or treatment of low-density lipoprotein (LDL) cholesterol-related diseases, in which the composition comprises a ribosome-binding agent.

Another purpose of the present disclosure is to provide a food composition for prevention or amelioration of low-density lipoprotein (LDL) cholesterol-related diseases, in which the composition comprises a ribosome-binding agent.

Still another object of the present disclosure is to provide a method for prevention or treatment of low-density lipoprotein (LDL) cholesterol-related diseases, in which the method comprises administering a composition comprising a ribosome-binding agent to a subject in need thereof.

Technical Solution

One aspect of the present disclosure provides a pharmaceutical composition for prevention or treatment of low-density lipoprotein (LDL) cholesterol-related diseases, in which the composition comprises a ribosome-binding agent.

Another aspect of the present disclosure provides a food composition for prevention or amelioration of low-density lipoprotein (LDL) cholesterol-related diseases, in which the composition comprises a ribosome-binding agent.

Still another aspect of the present disclosure provides a method for prevention or treatment of low-density lipoprotein (LDL) cholesterol-related diseases, in which the method comprises administering a composition comprising a ribosome-binding agent to a subject in need thereof.

Advantageous Effects

The ribosome-binding agent according to the present disclosure selectively increases the expression of LDL receptor in intestinal epithelial cells. This may promote absorption of LDL from blood and tissue, thereby reducing a level of LDL in a blood. Therefore, the ribosome-binding agent may be used to effectively prevent or treat the various LDL-related diseases including hyper low-density lipoprotein (LDL) cholesterinosis, hyperlipidemia, hypertension, and stroke.

MODES OF THE INVENTION

Figure 1A:
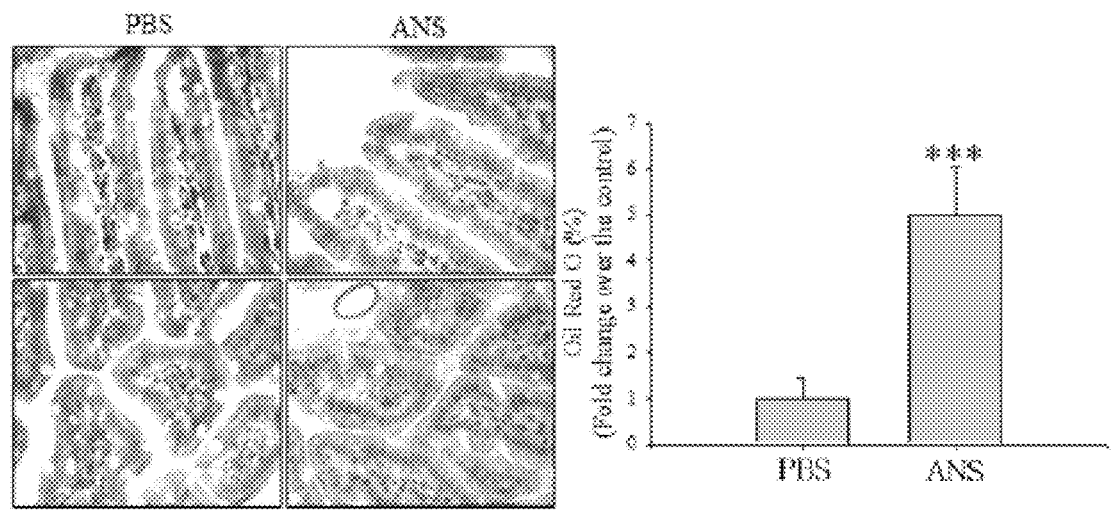
FIG. 1A illustrates checking results of lipid droplets from intestinal cells of ANS-fed mice via Oil Red O staining.

The present disclosure is described in detail below.

The present disclosure provides a pharmaceutical composition for the prevention or treatment of low-density lipoprotein (LDL) cholesterol-related diseases, in which the composition comprises a ribosome-binding agent.

Further, the present disclosure provides a method for prevention or treatment of low-density lipoprotein (LDL) cholesterol-related diseases, in which the method comprises administering the composition comprising the ribosome-binding agent described above to a subject in need thereof.

The subject refers to a bio entity that already has low-density lipoprotein (LDL) cholesterol-related disease or has a high possibility of having the low-density lipoprotein (LDL) cholesterol-related disease.

According to the present disclosure, the ribosome-binding agent refers to a substance that binds to the ribosome and inactivates the ribosome. The ribosome-binding agent may unlimitedly include a substance that acts to induce a stress due to inactivation of the ribosome within a cell.

The ribosome-binding agent may be at least one selected from a group consisting of deoxynivalenol (DON), anisomycin (ANS), 15-acetyl deoxynivalenol (15AcDON), nivalenol (NIV), T-2 toxin, trichothecenes, shiga toxin, shiga-like toxins, palytoxin, yessotoxin, ricin, puromycin, cycloheximide, emetine, gougerotin, RCA60, a-sarcin, pseudomonas exotoxin A, and diphtheria toxin. In one example, the ribosome-binding agent may be deoxynivalenol (DON), or anisomycin (ANS).

When the ribosome-binding agent is administered, an expression of the LDL receptor in the intestinal epithelial cells is selectively increased to promote the absorption of LDL in the blood and tissue, thereby reducing the level of LDL in the blood. In this way, it is possible to effectively prevent or treat various low-density lipoprotein (LDL) cholesterol-related diseases.

The pharmaceutical composition according to the present disclosure may include other ingredients which may, in addition to the ribosome-binding agent, have a synergistic effect on the main effect intended by the present disclosure, to the extent that the intended primary effect of the present disclosure is available.

Further, in accordance with the present disclosure, the pharmaceutical composition may further include, in addition to the active ingredients as described above, pharmaceutically acceptable carriers, excipients and diluents for administration of the composition.

For example, the carrier, excipient and diluent may be selected from the group consisting of lactose, textolose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil.

The pharmaceutical composition according to the present disclosure may be prepared in a variety of parenteral or oral dosage forms according to known methods. Representative examples of formulations for parenteral administration may include aerosol formulations, injectable formulations. Preferably, the pharmaceutical composition according to the present disclosure may be prepared in a form for oral administration.

Solid preparations for oral administration include tablets, pills, powders, granules, capsules and the like. Such a solid preparation may be prepared by mixing at least one or more excipients such as starch, calcium carbonate, sucrose or lactose, and gelatin with the above-mentioned active ingredients. Further, in addition to the simple excipients, lubricants such as magnesium stearate, talc may also be used.

Liquid preparations for oral administration include suspensions, solutions, emulsions, syrups and the like. The liquid preparation may include various excipients such as a wetting agent, a sweetening agent, a fragrance, and a preservative in addition to water and liquid paraffin which are commonly used simple diluents.

An effective dosage of the pharmaceutical composition according to the present disclosure may vary depending on the patient's age, gender, and weight. In one example, the composition may be administered at a dose of 0.0001 to 50 mg/kg, preferably 0.001 to 10 mg/kg.

The composition according to the present disclosure may be used alone or in combination with following methods for the prevention or treatment of the low-density lipoprotein (LDL) cholesterol-related disease: methods of using surgery, chemotherapy, radiotherapy, hormone therapy, drug therapy and biological response modifiers.

According to the present disclosure, the low-density lipoprotein (LDL) cholesterol-related disease refers to a disease caused by an increase in the concentration of low-density lipoprotein (LDL) in the blood. Examples of such diseases may include metabolic diseases such as obesity, fatty liver, diabetes, hyperlipidemia, hypertension, hypercholesterolemia, and hyper low-density lipoprotein (LDL) cholesterinosis, and cardiovascular disease and arteriosclerosis, and coronary artery disease. In the present disclosure, the cardiovascular disease or coronary artery disease refers to a disease caused by an increase in the level of the low-density lipoprotein (LDL) in the blood.

Therefore, according to the present disclosure, the low-density lipoprotein (LDL) cholesterol-related disease treatable by the ribosome-binding agent may include at least one selected from the group consisting of obesity, fatty liver, diabetes, hyperlipidemia, hypertension, hypercholesterolemia, hyper low-density lipoprotein, cardiovascular disease, arteriosclerosis, coronary artery disease, lipid metabolic disease, and lifestyle disease. Preferably, the low-density lipoprotein (LDL) cholesterol-related disease treatable by the ribosome-binding agent may be, but is not limited to, the hyper low-density lipoprotein (LDL) cholesterinosis.

The term "prevention" used in the present disclosure means any action that inhibits or slows down a progression of the low-density lipoprotein (LDL) cholesterol-related disease via administration of the composition according to the present disclosure.

The term "treatment" as used in the present disclosure refers to all actions including improvement of the low-density lipoprotein (LDL) cholesterol-related disease or alteration thereof to a favorable state via the administration of the composition according to the present disclosure.

Further, the present disclosure provides a food composition for the prevention or amelioration of low-density lipoprotein (LDL) cholesterol-related disease, in which the composition comprises a ribosome-binding agent.

The ribosome-binding agent according to the present disclosure may be used in health functional foods, food additives or dietary supplements.

When the ribosome-binding agent according to the present disclosure is used as a food additive, the ribosome-binding agent may be added alone, or added together with other food or food ingredients, or may be suitably used according to conventional methods.

Further, it is clear that the amount of the ribosome-binding agent, which is the active ingredient, may be appropriately changed depending on the intended use (prevention, health or therapeutic treatment). Preferably, the ribosome-binding agent may be included in a range of from 0.01 to 95% by weight based on a total weight of the food composition. More preferably, the ribosome-binding agent may be included in a range from 1 to 80% by weight based on the total weight of the food composition. In a specific example, the ribosome-binding agent in accordance with the present disclosure may be added in an amount of not more than 15% by weight, preferably not more than 10% by weight based on a total weight of the raw material in the production of food or beverages.

The type of the food is not particularly limited. Examples of foods adapted to include the ribosome-binding agent according to the present disclosure include meat, sausage, bread, chocolate, candy, snacks, confectionery, pizza, ramen, other noodles, gums, dairy products that contain ice cream, various soups, beverages, tea, drinks, alcoholic beverages, vitamin complexes, etc. The food includes all of the health food in a conventional sense.

When the food composition according to the present disclosure is manufactured as a beverage, the food composition may also include additional ingredients such as various flavors or natural carbohydrates, like ordinary beverages. The natural carbohydrate may include monosaccharides such as glucose and fructose, disaccharides such as maltose and sucrose, natural sweeteners such as dextrin and cyclodextrin, and synthetic sweetening agents such as saccharine and aspartame. The natural carbohydrate may be included in a range from 0.01 to 10% by weight, preferably from 0.01 to 0.1% by weight, based on the total weight of the food composition according to the present disclosure.

The food composition according to the present disclosure may include various nutrients, vitamins, electrolytes, flavors, colorants, pectic acid and its salts, alginic acid and its salts, organic acids, protective colloid thickening agents, pH adjusters, stabilizers, preservatives, glycerin, alcohols, carbonating agents used in carbonated drinks, etc. The food composition may also include, but is not limited to, fruits for the production of natural fruit juices, fruit juice drinks and vegetable drinks. These components may be used independently or in combination with each other. Although the content of the additives is not limited to a specific range, preferably, the additive content may be included in a range of 0.01 to 0.1% by weight based on the total weight of the food composition according to the present disclosure.

In the case of long-term ingestion of the food composition according to the present disclosure for the purposes of health and hygiene, or for the purpose of controlling health, the food composition according to the present disclosure has no problem in terms of safety. This long-term administration may be safe.

Terms not otherwise defined herein have the meanings commonly used in the art to which the present disclosure belongs.

Hereinafter, the present disclosure will be described in detail by Examples. However, Example is only an example of the present disclosure, and the content of the present disclosure is not limited to Example.

Example 1: Confirmation of Intracellular
Accumulation of Cholesterol Via Use of
Ribosome-Binding Chemical Agents for
Inactivation of the Ribosome The present inventors have examined to identify the effects of ribosome inactivation on the fat accumulation in vivo and in vitro.

1-1. In-Vivo

Six-week-old male B6C3F1 mouse (C57Bl/6J×C3H/HeJ) was purchased from Samtako Bio Korea (Osan, South Korea) for use in experiments to confirm the effect of the ribosome inactivation on fat accumulation. Animal experiments were carried out by animal testing methods as approved by the Laboratory Animal Care Committee (PNU-2010-0291).

Vehicle, 25 mg/kg anisomycin (ANS) or deoxynivalenol (DON) was administered to the mouse via oral gavage. After 24 hours, immunohistochemistry (IHC) was performed to measure a lipid level, a total cholesterol level and a low-density lipoprotein (LDL) level in a mouse enterocyte.

Lipid droplets in mouse small intestinal cells were stained via Oil Red O staining and the lipid droplets thus stained were observed with a 400× magnification microscope.

Figure 1B:
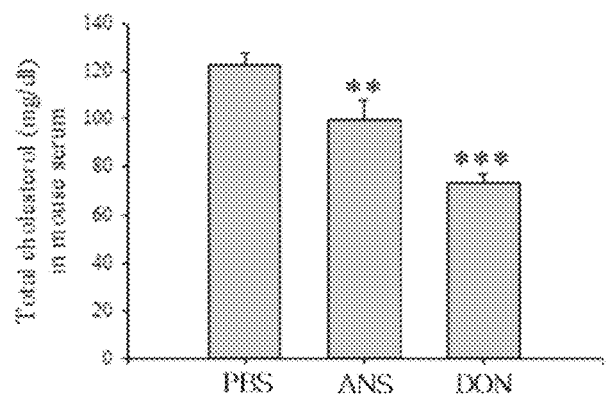
FIG. 1B illustrates results of measuring a total cholesterol level in serum after DON or ANS treatment thereof.
Figure 1C:
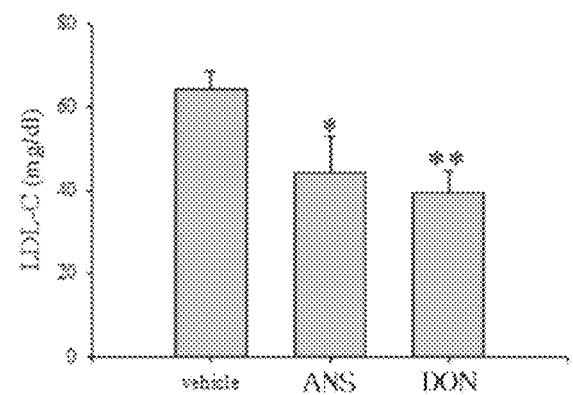
FIG. 1C illustrates results of measuring a LDL-C level in serum after DON or ANS treatment thereof.

From the result, as illustrated in FIG. 1, fat accumulation in intestinal tissue was increased in the experimental group. To the contrary, a total cholesterol level in serum (FIG. 1B) and a low-density lipoprotein (LDL) level (FIG. 1C) in serum were decreased.

1-2. In Vitro

To confirm the effect of ribosome inactivation on fat accumulation, enterocyte and hepatocyte exposed to ribosome inactivation stress using the ribosome-binding agent were stained with Oil Red O.

Specifically, HCT-8 cells and HepG2 cells were obtained from the American Type Culture Collection (ATCC Rockville, Md., USA). HCT-8 and HepG2 cells were treated with vehicle, 1000 mg/ml deoxynivalenol (DON), or 2 µM anisomycin (ANS) for 24 h. Lipid droplets in the HCT-8 and HepG2 cells were stained with Oil Red O and then the stained lipid droplets were observed with an ×200 magnification microscope. The staining results of HCT-8 cells are illustrated in FIG. 2 and the staining results of HepG2 cells are illustrated in FIG. 3.

Figure 2:
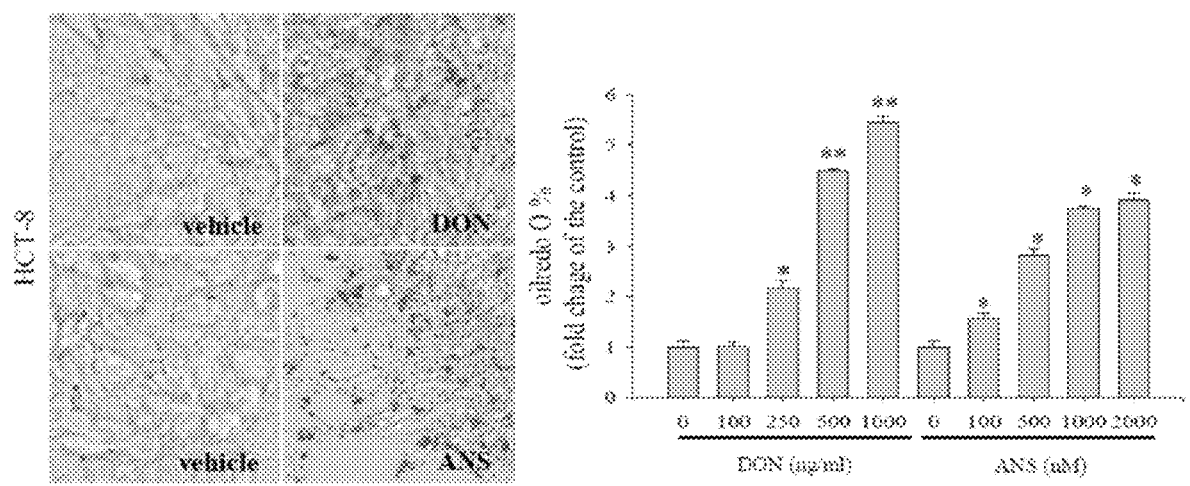
FIG. 2 illustrates results of checking lipid droplets from HCT-8 cells after DON and ANS treatment thereof via Oil Red O staining.
Figure 3:
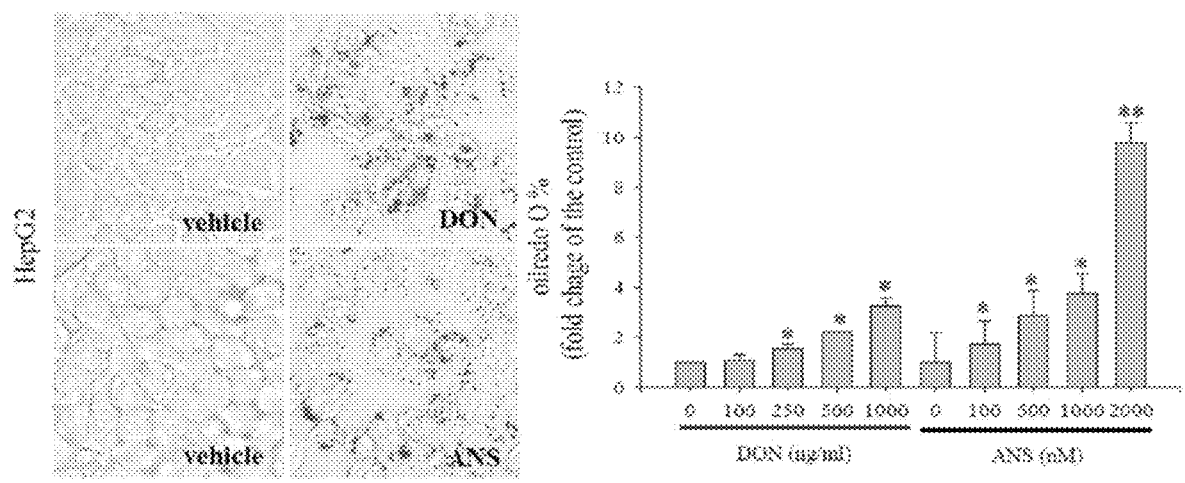
FIG. 3 illustrates results of checking lipid droplets from HepG2 cells after DON and ANS treatment thereof via Oil Red O staining.

As illustrated in FIG. 2, it was confirmed that intestinal pathogenic ribosome stress agents such as deoxynivalenol (DON) and anisomycin (ANS) dose-dependently increased fat accumulation in HCT-8 cells. Further, as illustrated in FIG. 3, fat accumulation was confirmed as a result of the response to chemical ribosome inactivation in HepG2 hepatocytes derived from human liver, as another organ that regulates cholesterol. Furthermore, it was confirmed that the fat was accumulated in a dose-dependent manner.

Further, HCT-8 cells and HepG2 cells were treated with the DON and ANS as chemical ribosome inactivators for 24 hours. Then, the treated cells were treated with filipin. Therefore, results of specific staining of cholesterol in the cells are illustrated in FIG. 4.

Figure 4:
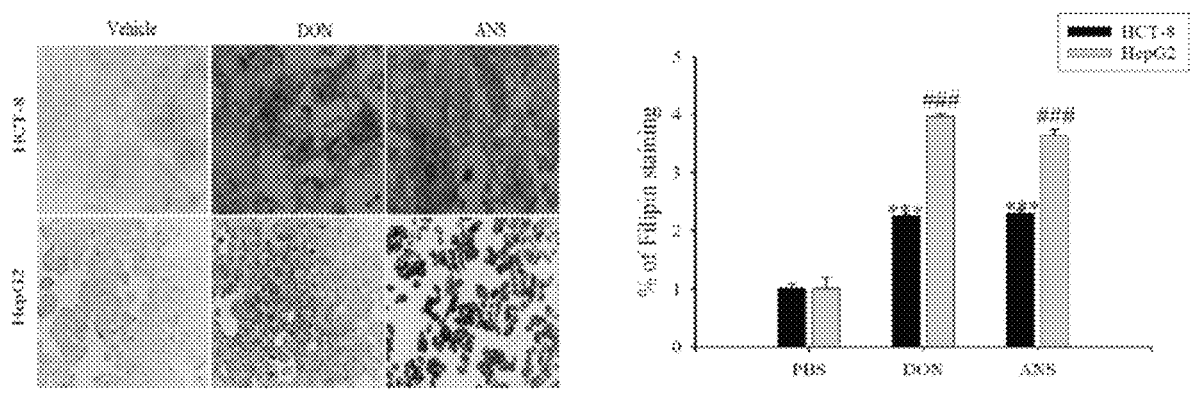
FIG. 4 illustrates results of checking cholesterol from HCT-8 cells and HepG2 cells after DON and ANS treatment thereof via filipin.

As illustrated in FIG. 4, the ribosome inactivation from the ribosome-binding agent treatment significantly increased a cholesterol accumulation level in the enterocyte and hepatocyte. Therefore, it was further confirmed that intracellular fat accumulation was induced in a response to the ribosome inactivation stress.

Further, HCT-8 cells and HepG2 cells were treated with vehicle, 1000 ng/ml DON, or 2 µM ANS for 48 hours. The thus treated cells were observed using a transmission electron microscope (TEM) at ×10,000 magnification. The results are illustrated in FIG. 5.

Figure 5:
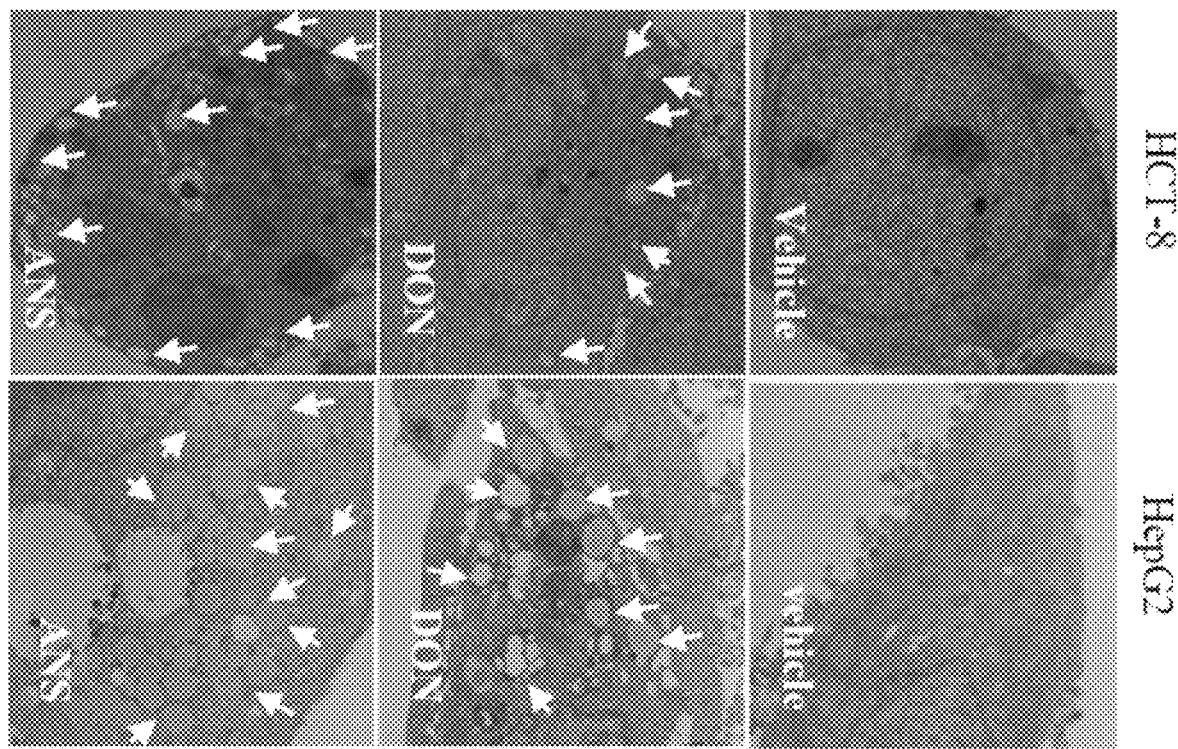
FIG. 5 illustrates results of checking cholesterol change from HCT-8 cells and HepG2 cells after DON and ANS treatment thereof via TEM.

As illustrated in FIG. 5, an arrow indicates a lipid droplet in each cell. The ribosome inactivation increased the number of lipid droplets in the cells. Therefore, it was confirmed that the ribosome inactivation was associated with pathogenesis associated with lipotoxicity.

Therefore, it was confirmed that the ribosome inactivation stress improves the absorption of cholesterol into cells.

Figure 6:
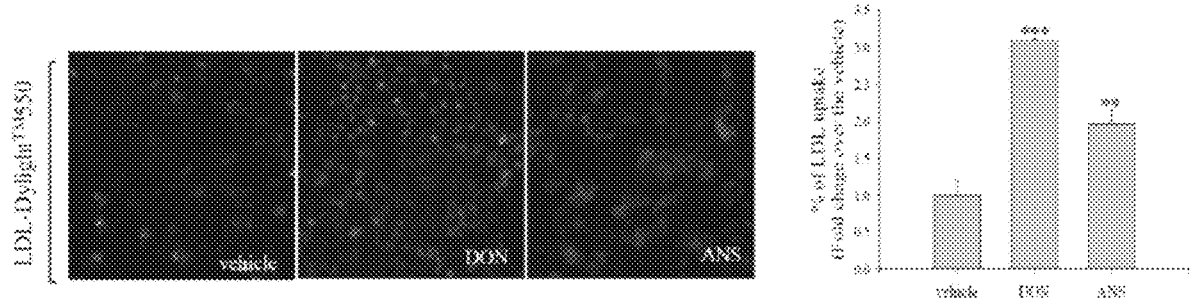
FIG. 6 illustrates results of checking LDL absorption from HCT-8 cells after DON and ANS treatment thereof via LDL-Dylight™ 550 staining.

Example 2: Confirmation that Cholesterol Absorption is Mediated by Intracellular LDL Receptor The present inventors measured a level of LDL-cholesterol absorption via LDLR (LDL receptor) in enterocytes in order to confirm intracellular cholesterol accumulation. HCT-8 cells were treated with vehicle, 1000 ng/ml DON, or 2 µM ANS for 24 hours. To visualize the LDL absorption, the cells thus treated were stained with LDL-Dylight™ 550 (red). The results are illustrated in FIG. 6. To visualize LDLR expression, the cells thus treated were stained with DyLight™ 488-conjugated LDLR (green). The results are illustrated in FIG. 7.

Figure 7:
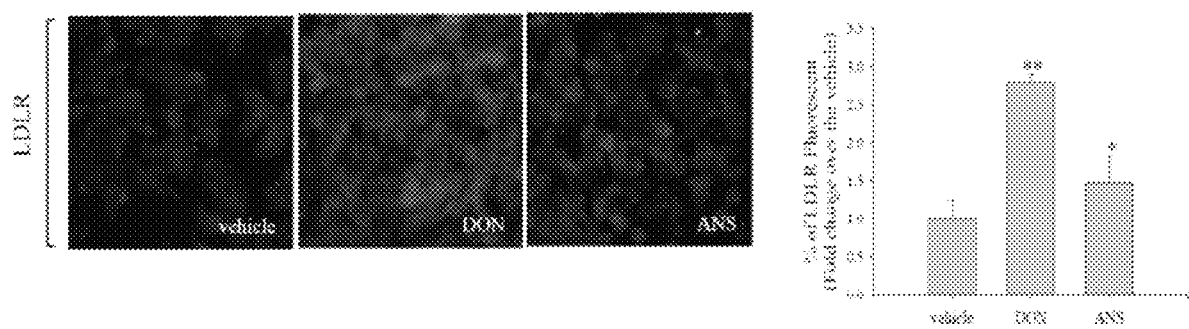
FIG. 7 illustrates results of checking LDL receptor expression from HCT-8 cells after DON and ANS treatment thereof via DyLight™-488-conjugated LDLR staining in order to visualize the LDL receptor expression.

As illustrated in FIG. 6 and FIG. 7, it was confirmed that the ribosome inactivation increases the extent of labeled exogenous LDL uptake into the enterocyte. Further, the LDLR expression was also significantly increased by the ribosome inactivation.

Therefore, the ribosome inactivation stress resulting from the treatment of the ribosome-binding agent may improve a LDL absorption level in cells and enhance a LDLR expression level in cells.

Figure 8:
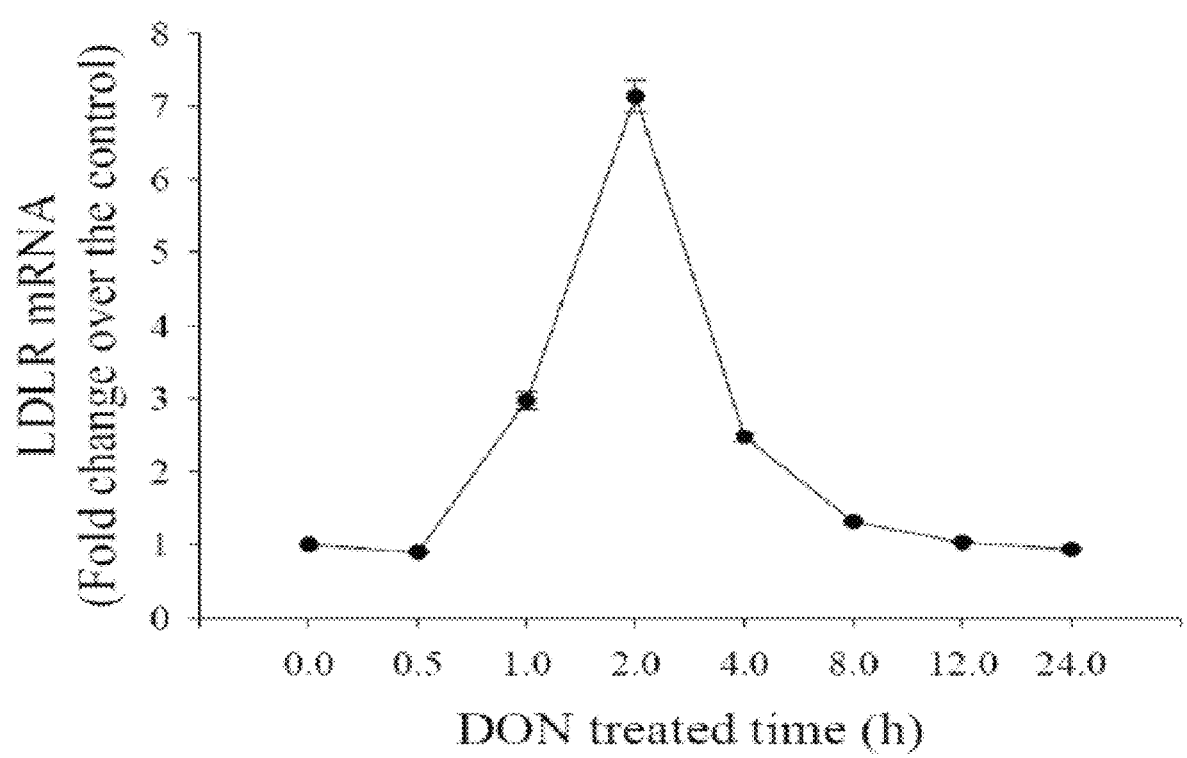
FIG. 8 illustrates results of checking of a mRNA level of a LDL receptor in HCT-8 cells after treatment with DON thereof via a real-time RT-PCR.

Further, HCT-8 cells were treated with vehicle or 1000 ng/ml DON for the indicated time. In these treated cells, an mRNA level of LDLR was measured using real-time RT-PCR. Specifically, RNA was extracted using RiboEX (Gene-All Biotechnology, Seoul, Korea). Subsequently, the RNA (100 ng) from each sample was transcribed into cDNA using Prime Moloney murine leukemia virus reverse transcriptase (Genetbio, Nonsan, South Korea). The cDNA was then amplified using n-Taq DNA polymerase (Enzynomics, Seoul, South Korea). The amplified cDNA was treated at 95° C. for 2 minutes. The cDNA was then treated for 30 seconds at 95° C., for 30 seconds at 58° C. and for 30 seconds at 72° C. at each of different cycles. The thus treated cDNA was amplified and the amplification thereof was confirmed by electrophoresis. FAM was used as a fluorescent reporter staining drug. FAM was conjugated to a 5' terminal of a product of the amplified cDNA. The resulting product was subjected to real-time RT-PCR using an iCycler thermal cycler (Bio-Rad). The results are illustrated in FIG. 8.

Figure 9:
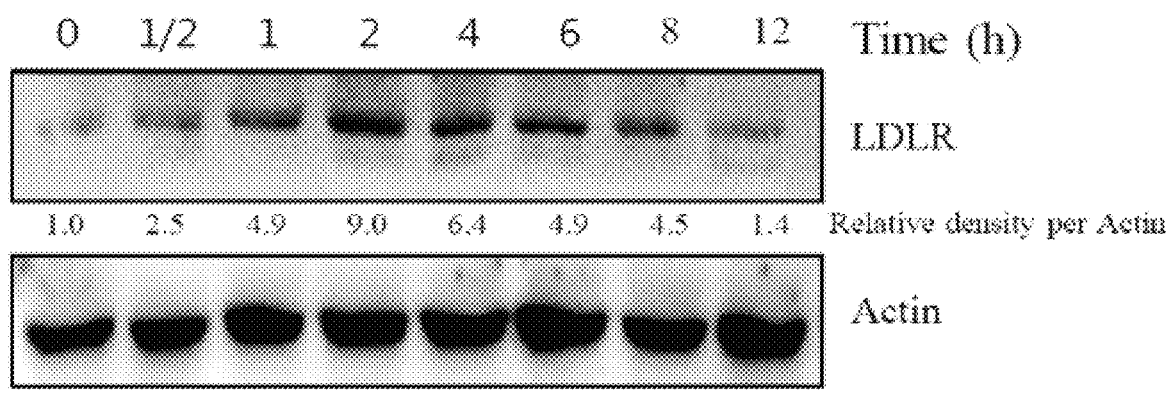
FIG. 9 illustrates results of checking of a protein level of a LDL receptor in HCT-8 cells after treatment with DON thereof via a Western blot.

Further, HCT-8 cells were treated with vehicle or 1000 ng/ml DON for the indicated time. Thereafter, protein levels of LDLR were measured using whole cell lysates via Western blots. Specifically, the cells were washed with phosphate buffer. Subsequently, the cells were dissolved in lysis buffer (1% [w/v] SDS, 1.0 mM sodium orthovanadate, and 10 mM Tris [pH 7.4]). The lysate was sonicated for 5 seconds. The lysate was quantitated using the BCA protein assay kit (Pierce, Rockford, Ill., USA). Subsequently, immunoblotting was carried out to confirm the level of the protein in the cells. The results are illustrated in FIG. 9.

Figure 10:
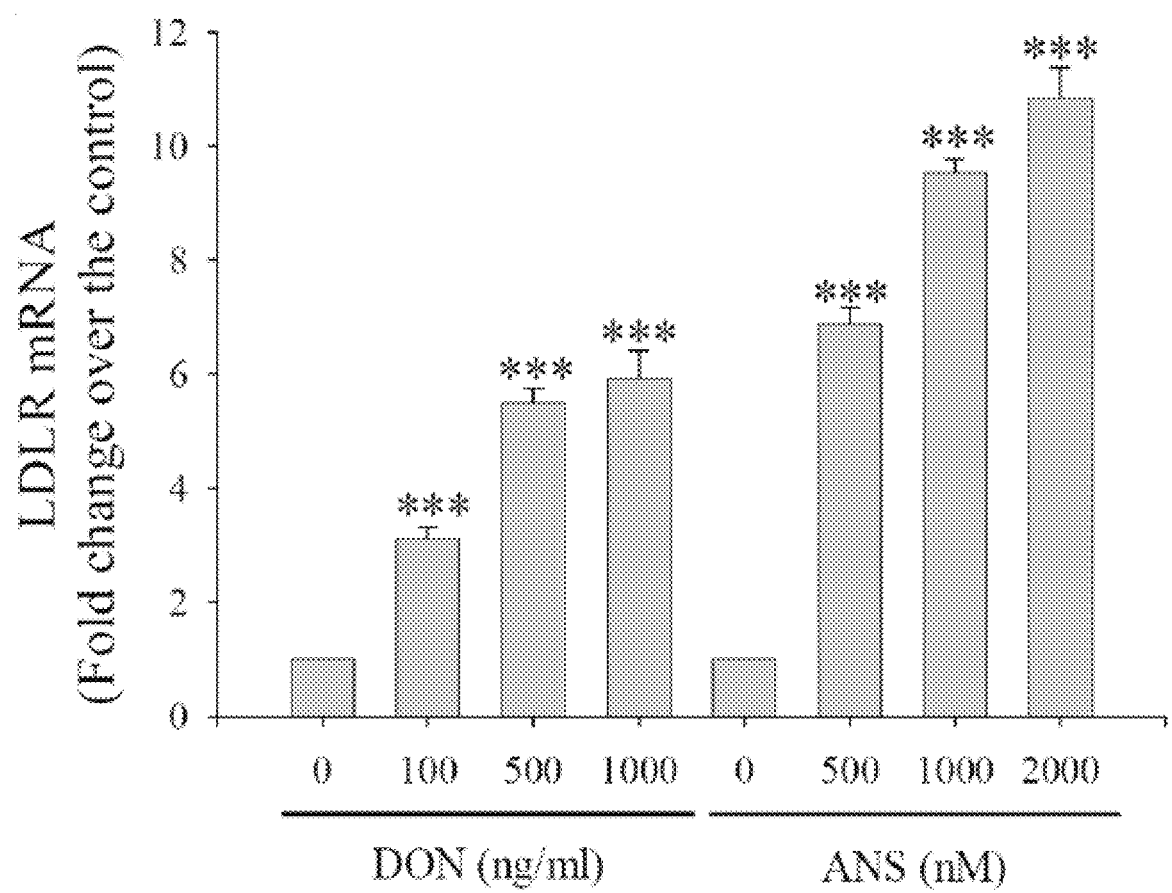
FIG. 10 illustrates results of checking of an mRNA level of a LDL receptor in HCT-8 cells after treatment with DON and ANS at various contents via a real-time RT-PCR.

Additionally, to determine the effect of chemical ribosome inactivators (DON, ANS) at different doses on the LDLR expression level, HCT-8 cells were treated with vehicle, 0, 100, 500, 1000 ng/ml DON or 0, 500, 1000, 2000 nM ANS for 2 hours. Then, mRNA levels of LDLR in the cells were measured using real-time RT-PCR. The results are illustrated in FIG. 10. HepG2 cells were similarly treated for 1 hour with 0, 100, 500, 1000 ng/ml DON or 0, 500, 1000, 2000 nM ANS. The mRNA level of the LDLR of the cells was measured. The results are illustrated in FIG. 11.

Figure 11:
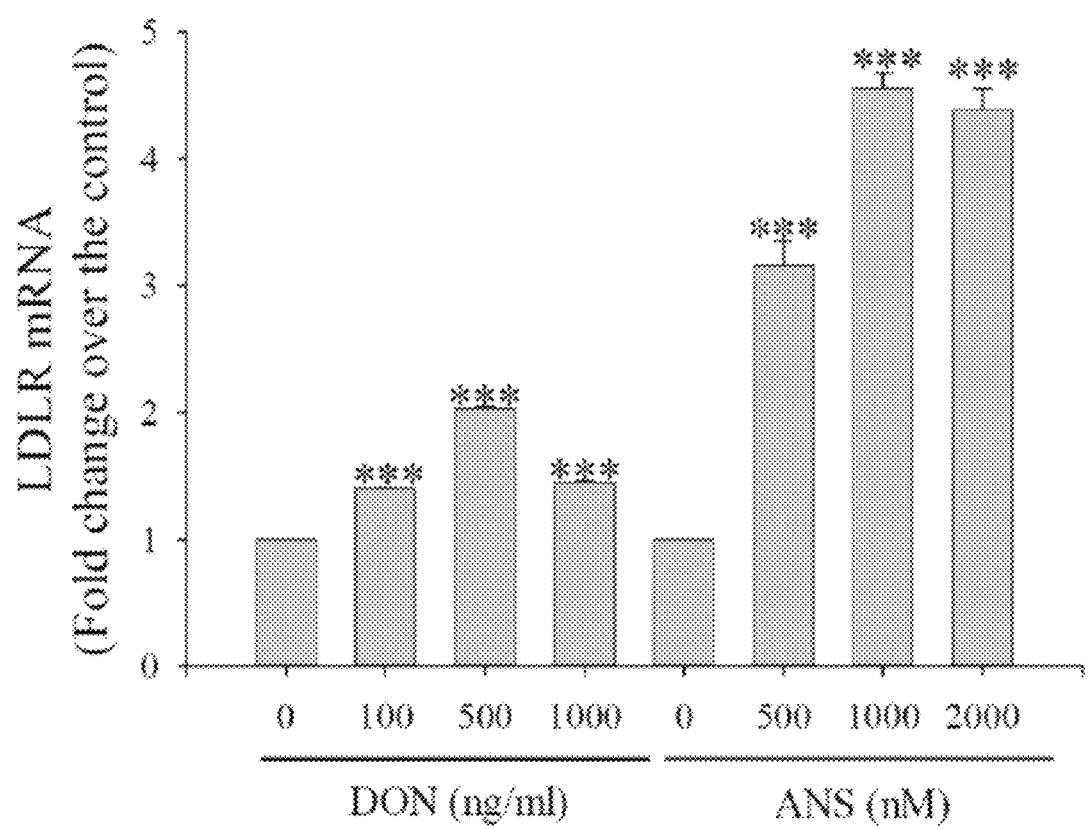
FIG. 11 illustrates results of checking of an mRNA level of a LDL receptor in HepG2 cells after treatment with DON and ANS at various contents via a real-time RT-PCR.

As illustrated in FIG. 10 and FIG. 11, it was confirmed that treatment of DON and ANS as ribosome-binding agents increases mRNA and protein levels of LDLR. It was confirmed that this increase is dependent on the doses of DON and ANS.

Further, additional animal studies were performed to determine whether ribosome-inactivation stress increases a level of LDLR expression in the small intestine. Six-week-old male B6C3F1 mice (C57Bl/6J×C3H/HeJ) were purchased from Samtako Bio Korea (Osan, South Korea). Animal experiments were performed according to the animal test method as approved in the Laboratory Animal Care Committee (PNU-2010-0291). Vehicle or 25 mg/kg DON was administered to the mice via oral feeding. After 24 hours, immunohistochemistry (IHC) was performed on ileum and jejunum to measure LDLR expression levels. The results are illustrated in FIG. 12.

Figure 12:
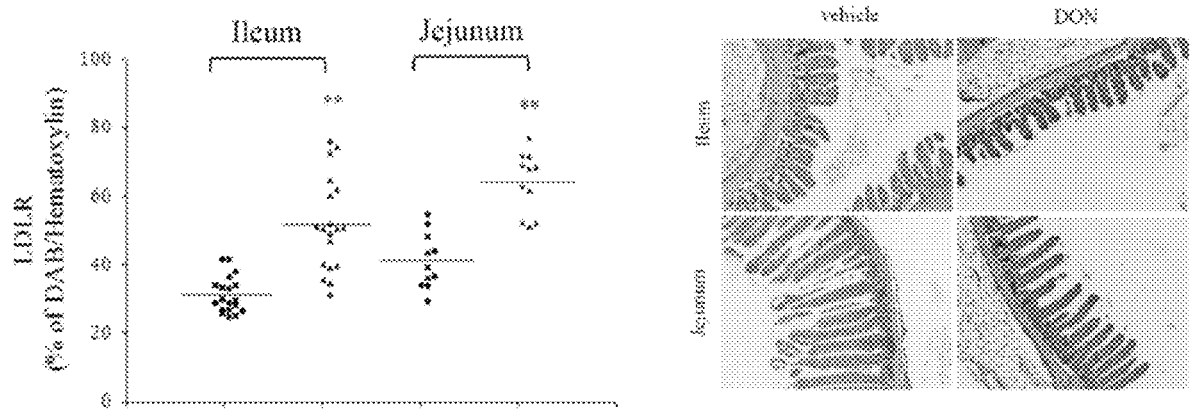
FIG. 12 illustrates results of immunohistochemistry for the LDL receptor in jejunum and ileum of a mouse fed with DON.

As illustrated in FIG. 12, when DON as a ribosome-binding agent was administered to the mice via oral feeding, an increase in the level of LDLR expression was observed in the mouse small intestine. In particular, it was confirmed that the expression of LDLR was increased in villus epithelium of ileum and jejunum.

Further, to further confirm whether the accumulation of fat induced by ribosome inactivation depends on LDLR-mediated cholesterol absorption, ShRNA for LDLR was used. ShRNAs were prepared by inserting shRNA templates into pSilencer 4.1-CMVneo vector (Ambion, Austin, Tex., USA). A plasmid with the shRNA for LDLR was designated as shLDLR. LDLR shRNA targeted 5'-GGA CAG ATA TCA TCA ACG A-3' (SEQ ID NO. 1) sequence. A plasmid (pLDLR 234-CRE-mutant) that includes the human LDLR promoter (+94 to +30) was obtained from Dr. JingwenLiu (Department of Veterans Affairs, Palo Alto Health Care System, Livermore, Calif., USA). HCT-8 cells and HepG2 cells were treated with a mixture of plasmids using a jetPRIME transfection reagent (Polyplus-transfection, New York, N.Y., USA) according to the manufacturer's protocol. An efficiency of transfection was confirmed by expression in the pMX-GFP vector. At 4 hours after the transfection, a medium was changed and the cells were again cultured for 48 hours.

Figure 13:
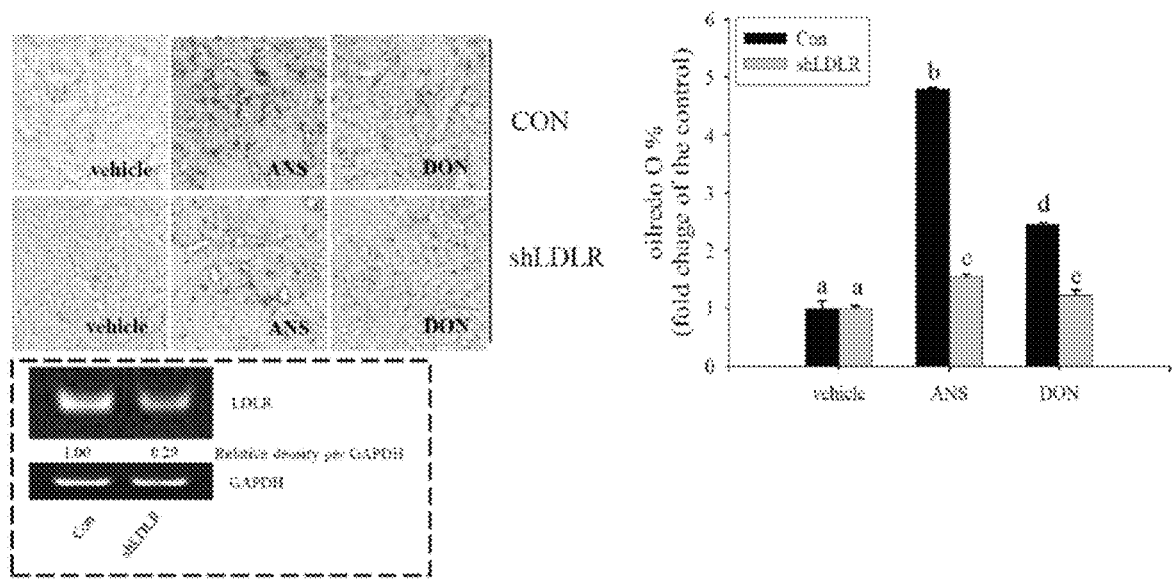
FIG. 13 illustrates results of checking lipid droplets in HCT-8 cells transfected with shRNA for a LDL receptor after treatment with DON and ANS thereof via Oil-Red O staining.

HCT-8 cells and HepG2 cells transfected with Empty vectors or shLDLR for LDLR were treated with vehicle, 1000 ng/ml DON, or 2 μM ANS. Lipid droplets in the cells were stained via Oil Red O staining. The stained lipid droplet was observed with a 200× magnification microscope. The results for HCT-8 cells are illustrated in FIG. 13. The results for HepG2 cells are illustrated in FIG. 14.

Figure 14:
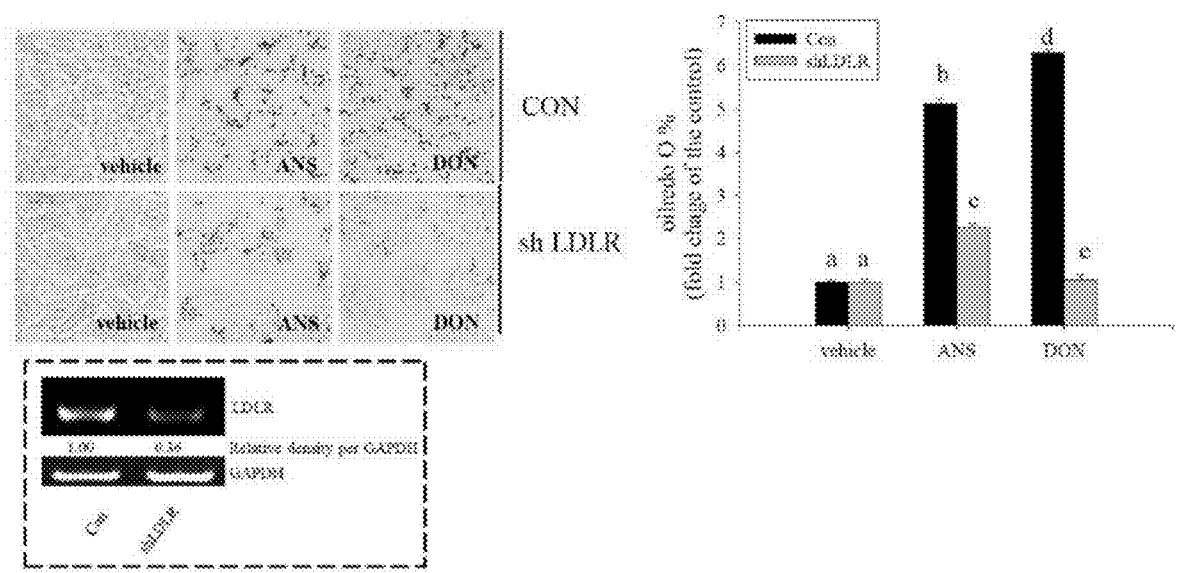
FIG. 14 illustrates results of checking lipid droplets in HepG2 cells transfected with shRNA for a LDL receptor after treatment with DON and ANS thereof via Oil-Red O staining.

As illustrated in FIG. 13 and FIG. 14, the expression of LDLR was inhibited by shRNA for LDLR. It was confirmed that lipid accumulation in enterocyte and hepatocyte was significantly decreased due to inhibition of LDLR expression.

Therefore, the ribosome inactivation improves the intracellular uptake of cholesterol. It was confirmed that because the improvement of the intracellular uptake of cholesterol is mediated by LDLR, LDLR expression in human enterocytes and hepatocytes increases lipid accumulation.

While the present disclosure has been described with reference to the above-described preferred examples, various modifications and variations may be made without departing from the spirit and scope of the present disclosure. It is also to be understood that the appended claims are intended to cover such modifications or changes as fall within the gist of the present disclosure.

The invention claimed is:

1. A method for treatment of a Low-Density Lipoprotein cholesterol-related disease, comprising administering a composition comprising deoxynivalenol to a subject in need thereof, wherein the Low-Density Lipoprotein cholesterol-related disease comprises at least one selected from the group consisting of Hyperlipidemia, Hypercholesterolemia, and Hyper Low-Density Lipoprotein Cholesterinosis.

2. The method of claim 1, wherein the composition is for oral administration.

3. The method of claim 1, wherein the deoxynivalenol increases an expression of a Low-Density Lipoprotein receptor.

* * * * *